United States Patent [19]

Sato et al.

[11] Patent Number: 4,532,308
[45] Date of Patent: Jul. 30, 1985

[54] EPOXY RESIN COMPOSITION

[75] Inventors: Tadahide Sato; Kuniaki Tobukuro, both of Shiga; Tosio Sugimoto, Mie; Kaoru Kanayama, Ibaraki, all of Japan

[73] Assignees: Mitsubishi Petrochemical Co., Ltd.; Mitsubishi Yuka Fine Chemicals Co., Ltd.; Toray Industries, Inc., all of Tokyo, Japan

[21] Appl. No.: 633,925

[22] Filed: Jul. 24, 1984

[30] Foreign Application Priority Data

Aug. 11, 1983 [JP] Japan ................ 58-145677

[51] Int. Cl.³ .................................. C08G 59/26
[52] U.S. Cl. ...................... 525/482; 528/96; 528/99; 528/102; 528/103
[58] Field of Search ............ 528/96, 99, 102, 103; 525/482

[56] References Cited

U.S. PATENT DOCUMENTS

| | | | |
|---|---|---|---|
| 3,320,208 | 5/1967 | Mange | 528/96 |
| 3,388,098 | 6/1968 | Harding | 528/96 |
| 3,401,147 | 9/1968 | Smith et al. | 528/96 |

Primary Examiner—Earl A. Nielsen

Attorney, Agent, or Firm—Oblon, Fisher, Spivak, McClelland & Maier

EXEMPLARY CLAIM

1. An epoxy resin composition is described, comprising (1) a mixture of epoxides of Components (A), (B) and (C)

Component (A):
20 to 60 wt % of an epoxy compound having a spiroacetal ring represented by the formula:

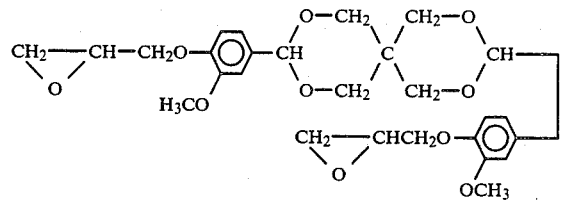

Component (B):
10 to 50 wt % of a brominated epoxy resin

Component (C):
10 to 50 wt % of an epoxy resin selected from the group consisting of diglycidyl ether of bisphenol A, diglycidyl ether of bisphenol F, novolac type epoxy resins and N,N,O-triglycidyl-aminophenol type epoxy resins, and (2) a hardening agent.

3 Claims, No Drawings

EPOXY RESIN COMPOSITION

FIELD OF THE INVENTION

The present invention relates to an epoxy resin composition for carbon fiber reinforcement which has excellent elongation, heat resistance and modulus of elasticity and provides a hardened product having a low water absorbability.

BACKGROUND OF THE INVENTION

Epoxy resin have been widely employed in the fields of adhesives for paint, sealing agents, structural materials, etc. due to their excellent heat resistance, electrically insulating property, chemical resistance and mechanical characteristics. Particularly, composite materials reinforced with carbon fibers (CFRP) have been recently employed as structural materials for space- and air-crafts, base materials for transportation industries such as railways and automobiles, etc., materials for leisures such as golf shafts, rods, ski boards, etc. because CRFP possess mechanical strength and modulus of elasticity which are equivalent to or stronger than those of metals and can render the weight light. Thus, great developments are further expected.

At present, polyepoxy compounds which are employd as matrix resins for CFRP include diglycidyl ether of bisphenol A (Epicoat 828, Epicoat 1004, etc.; Yuka Shell Epoxy Co., Ltd., trademarks), polyepoxide of aminophenol (ELF-120; Sumitomo Chemical Co., Ltd., trademark), tetraepoxide of methylenedianiline (YH-434, Toto Kasei Co,. Ltd., trademark), phenol novolac polyepoxide (Epicoat 154; Yuka Shell Epoxy Co., Ltd., trademark), ortho-cresol novolac epoxide (EOCN 104 S: Nippon kayaku Co., Ltd., trademark), etc.

However, CFRP in which these polyepoxy compounds are used as matrix resins are not sufficiently satisfied with performances such as elongation (flexibility), heat resistance, modulus of elasticity, low water absorbability etc., which are required in large scale elements such as primary structural materials, etc. for aircrafts.

A polyepoxy compound having a spiroacetal ring is known as an polyepoxy compound which gives hardened product having good flexibility.

For example, U.S. Pat. No. 3,128,225 discloses a polyepoxy compound represented by the formula:

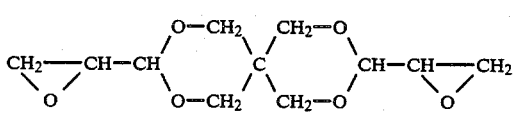

However, the thermal distortion temperature of the hardened product obtained therefrom is in the range of 147° to 170° C., which is poor in heat resistance as matrix resins for use of primary structural materials for aircrafts.

Further, U.S. Pat. Nos. 3,347,871 and 3,388,098 disclose a polyepoxy compound represented by the formula:

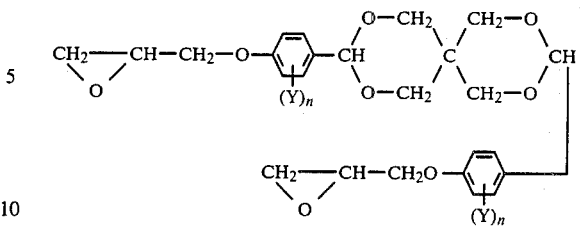

wherein Y is H, Cl or $CH_3$ and n is 0 or an integer of 1 or 2, which is produced by (A) reacting a monovalent phenol having an aldehyde group at the p-position to the phenolic hydroxy group with pentaerythritol and then (B) reacting epichlorohydrin with the resulting divalent phenol. While this polyepoxy compound gives a hardened product having excellent heat resistance and impact resistance, it involves disadvantages that not only the compound is required to further improve the flexibility and the solubility in widely used solvents, e.g., acetone, methyl ethyl ketone, methyl isobutyl ketone, toluene, ethyl acetate, tetrahydrofuran, etc. is poor but also mixtures with other epoxy resins widely used cause phase separation due to its poor compatibility with these epoxy resins, e.g., diglycidyl ether of bisphenol A, novolac type epoxy resins, etc.

In order to overcome these problems, the present inventors have previously proposed the epoxy compound having the spiroacetal ring represented by the formula (I):

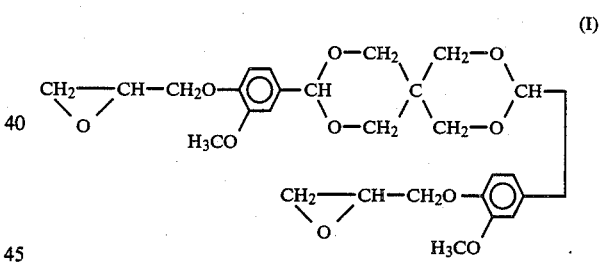

in Japanese Patent Application No. 21970/82.

The spiroacetal ring-containing epoxy compound has excellent solubility in solvents and gives a hardened product having excellent flexibility but is further required to improve a water absorption rate.

A high water absorption rate of the hardened product results in reduction of strength.

SUMMARY OF THE INVENTION

The present invention has been made to improve the disadvantages of such a spiroacetal ring-containing epoxy compound and the reduction of the water absorption rate is attempted by the use thereof in combination with a brominated epoxy resin.

Accordingly, an object of the present invention is to provide an epoxy resin composition comprising (1) a mixture of epoxides (A), (B) and (C).

Component (A):

20 to 60 wt% of an epoxy compound having a spiroacetal ring represented by the formula:

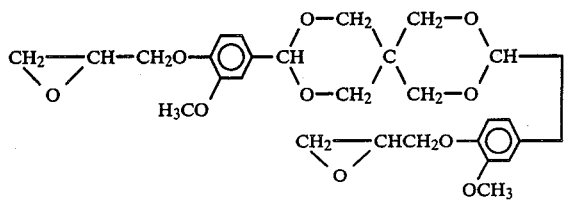

Component (B):
    20 to 60 wt% of a brominated epoxy resin
Component (C):
    10 to 50 wt% of an epoxy resin selected from the group consisting of diglycidyl ether of bisphenol A, diglycidyl ether of bisphenol F, novolac type epoxy resin and N,N,O-triglycidyl-aminophenol type epoxy resin, and
    (2) a hardening agent.

The spiroacetal ring-containing epoxy compound of Component (A) represented by the formula (I) of the present invention is prepared by reacting vanilin with pentaerythritol and then epoxydizing the resulting polyphenol using epichlorohydrin. In this case, a polymer represented by the following formula (II) is sometimes formed in an amount of 40 wt% or less.

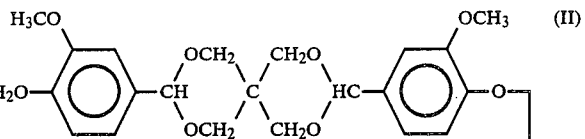

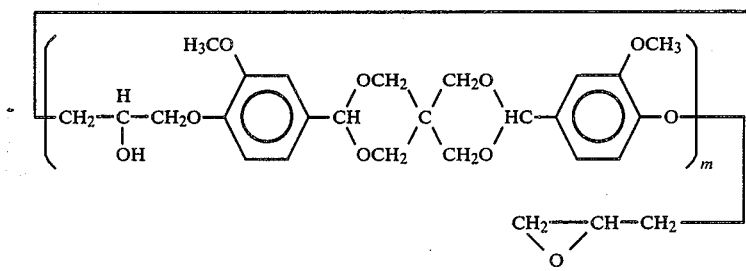

wherein m is 0.1 to 2.

The brominated epoxy resin of Component (B) contributes to decrease the water absorption rate of the hardened product. Examples of the brominated epoxy resin include diglycidyl ether of brominated bisphenol A, diglycidyl ether of brominated bisphenol F, brominated phenol novolac resin, brominated cresol novolac resin, etc.

The epoxy resin of Component (C) is used to decrease the viscosity of the composition thereby improving the mixing ability with fibers, inorganic powders, etc. (diglycidyl ether of bisphenol A or bisphenol F), improve the heat resistance of hardened product (phenol novolac epoxy resin, cresol novolac epoxy resins) and accelerate hardening ability of the composition (N,N,O-triglycidylaminophenol type epoxy resin). Of these components (C), polyepoxides showing liquid state at 20° C. are particularly preferred from a standpoint of workability.

Component (A) is used in an amount of 20 to 60 wt%, preferably 25 to 55 wt%, based on the weight of the epoxy resin components. If the amount is less than 20 wt%, the flexibility of the hardened product is not practical. On the other hand, if the amount exceeds 60 wt%, decrease in water absorption rate cannot be expected.

Component (B) is used in an amount of 10 to 50 wt%, preferably 20 to 35 wt%, based on the weight of the epoxy resin components. If the amount is 10 wt%, the effect of decreasing the water absorption rate cannot be expected. If the amount is more than 50 wt%, the flexibility of the hardened product is not practical. Further, component (B) precipitates so that there is a possibility of causing phase separation and at the same time, the adhesion with carbon fibers becomes poor.

Component (C) is used in an amount of 10 to 50 wt% based on the weight of the epoxy resin components. In the case of using diglycidyl ether of disphenol A or F or novolac type epoxy resins, however, the amount is not greater than 50 wt%. In the case of using N,N,O-triglycidyl-aminophenol type epoxy resins, the amount is not greater than 40 wt%.

Various hardening agents as used in conventional epoxy resins can be used as hardening agents for hardening these epoxy resins. Examples of the hardening agents include aliphatic amines, aromatic amines, heterocyclic amines, Lewis acids such as boron trifluoride, etc. and salts thereof, organic acids, organic acids anhydrides, urea or derivatives thereof and polymercaptans, etc. Specific examples of these hardening agents include aromatic amines such as diaminodiphenylmethane, diaminodiphenylsulfone, 2,4-diamino-m-xylene, etc.; imidazoles or substituted imidazoles such as 2-methylimidazole, 2,4,5-triphenylimidazole, 1-cyanoethyl-2-methylimidazole, etc., or salts thereof with organic acids; organic carboxylic acids such as fumaric acid, trimellitic acid, hexahydrophthalic acid, etc.; organic acid anhydrides such as phthalic anhydride, endomethylenetetrahydrophthalic anhydride, hexahydrophthalic anhydride, etc.; urea derivatives such as dicyandiamide, melamine, guanamine, etc.; aliphatic polyamines such as triethylenetetramine, diethylenetriamine, xylenediamine, isobrondiamine, etc. and addition products thereof with epoxy compounds such as ethylene oxides, propylene oxides, etc. or, with acyl compounds such as acrylonitrile, acrylic acid, etc.

Of these hardening agents, diaminodiphenylsulfone is particularly preferred because it gives the hardening product having excellent heat resistance and at the same time, it gives a composition having excellent storage stability.

The epoxy resin composition may further contain, in addition to the hardening agent, a various additives such as carbon fibers, glass fibers, plasticizers, organic solvents, reactive diluents, extenders, fillers, reinforcing agents, pigments, flame-resistant agents, thickners, accelerators, agents for imparting flexibility, etc., if necessary and desired. Typical examples of accelerators include heterocyclic amines, Lewis acids such boron trifluoride, etc. and salts thereof, organic acids, organic anhydrides, urea or derivatives thereof, and polymercaptans, etc.

The composition of the present invention has excellent solubility in organic solvents and the solution of the composition is useful as varnishes for immersing carbon fibers. Further, the hardened product obtained from the composition of the present invention is markedly superior in thermal properties such as flexibility, thermal distortion temperature, etc. as compared to conventional bisphenol type epoxy resins and also has mechanical properties comparable to or better than those of the conventional bisphenol type epoxy resins.

The present invention will be described in more detail by reference to the following examples.

Preparation of Epoxy Compound of Component A

Into a 1 liter four-necked flask equipped with a thermometer, a nitrogen-introducing tube, a stirring apparatus and a water separator were charged 152 g (1 mol) of 4-oxy-3-methoxybenzaldehyde, 68 g of pentaerythritol, 3.0 g of p-toluenesulfonic acid, 500 ml of toluene and 150 ml of N,N-dimethylformamide. While flowing a nitrogen gas in the system, the mixture was heated at 120° C. to effect dehydration condensation. The formed water was continuously removed by azeotropic distillation with toluene and the reaction was completed at the time when the formed water reached a theoretical amount (18 ml).

After completion of the reaction, the solution of the resulting product was poured into 5 liters of water. Crystals precipitated were taken out by filtration and dried to obtain 132.1 g (yield 65.4%) of 3,9-bis(4-oxy-3-methoxy-phenyl)-2,4,8,10-tetraoxaspiro 5.5 undecane as white crystals. The melting point of the crystals was 174° C.

Into a 1 liter three-necked flask of equipped with a thermometer, a cooler and a stirring apparatus were charged 202 g (0.5 mol) of 3,9-bis(4-oxy-3-methoxy-phenyl)-2,4,8,10-tetraoxaspiro 5.5 undecane obtained above, 462.5 g (5.0 mols) of epichlorohydrin and 4.0 g of tetramethylammonium bromide. The reaction was conducted for 2 hours under reflux (117° C.).

Then, the reaction solution was cooled to 60° C. After a water separator was equipped, 42 g (1.05 mol) of sodium hydroxide was added and cyclization was performed under reduced pressure (150 to 100 mmHg). The formed water was continuously removed by azeotropic distillation with epichlorohydrin out of the system and at the time when the formed water reached 18 ml, the reaction was completed.

After the unreacted epichlorohydrin was recovered at 60° to 110° C. under 0.1 to 50 mmHg, the product was rendered a slurry by adding 1 liter of methyl isobutyl ketone thereto. Then, the slurry was throughly washed with 500 ml of water to remove sodium chloride by-produced.

From the product solution after washing with water, methyl isobutyl ketone was remobed by distillation under reduced pressure using a rotary evaporator to obtain 284 g of a light yellow solid. The epoxy equivalent of the product was 290 and the softening point was 65° to 72° C.

EXAMPLE 1

An epoxy resin composition was prepared by blending 40 parts by weight of the spiroacetal ring-containing epoxy compound obtained in the above preparation example, 30 parts by weight of diglycidyl ether of bisphenol A "Epicoat 828" made by Yuka Shell Epoxy Co., Ltd. (trademark, epoxy equivalent: 187), 30 parts by weight of diglycidyl ether of bisphenol A "Epicoat 1050" made by Yuka Shell Epoxy Co., Ltd. (trademark, epoxy equivalent: 440, bromine content: 40%) and 23 parts by weight of diaminodiphenylsulfone.

The solubility of the composition in solvents is shown in Table 1. The composition was throughly mixed in a heated kneader, subjected to prehardening at 180° C. for 1 hour and then post-hardening at 190° C. for 4 hours to obtain a hardened product.

The glass transition point, modulus of elasticity, elongation and water absorption rate after immersing in boiled water for 20 hours, of the hardened product are shown in Table 1.

EXAMPLE 2 TO 6 AND COMPARISON EXAMPLE 1 TO 5

The epoxy resin compositions having compositions shown in Table 1 were prepared. The compositions were hardened in the same manner as in Example 1 to obtain hardened products.

The results are shown in Table 1. The abbreviations therein are as follows:

YX-7: Epoxy compound having the spiroacetal ring
E-828: Epicoat 828 (trademark)
E-1050: Epicoat 1050 (trademark)
E-154: Phenol novolac type epoxy resin "Epicoat 154" (trademark) made by Yuka Shell Epoxy Co., Ltd.
ELM-120: N,N,O-triglycidylmetaminophenol "Sumiepoxy ELM-120" (trademark), made by Sumitomo Chemical Industry Co., Ltd.
DDS: diaminodiphenylsulfone
BREN: Brominated phenol novolac epoxy resin (epoxy equivalent: 270 to 300) made by Nippon Kayaku Co., Ltd.
E-807: Diglycidyl ether of bisphenol F "Epicoat 807" (trademark, epoxy equivalent: 180) made by Yuka Shell Co., Ltd.

TABLE 1

| | Example | | | | | | Comparison Example | | | | |
|---|---|---|---|---|---|---|---|---|---|---|---|
| | 1 | 2 | 3 | 4 | 5 | 6 | 1 | 2 | 3 | 4 | 5 |
| Composition (parts by weight) | | | | | | | | | | | |
| (A) YX-7 | 40 | 40 | 50 | 40 | 30 | 55 | 100 | 20 | 60 | 50 | 80 |
| (B) E-1050 | 30 | 30 | 40 | | 30 | 20 | | | | 50 | 10 |
| BREN | | | | 15 | | | | | | | |
| (C) E-828 | 30 | 20 | | 45 | | 25 | | 80 | 40 | | 10 |
| E-807 | | | | | 40 | | | | | | |

TABLE 1-continued

|  | Example | | | | | | Comparison Example | | | | |
| --- | --- | --- | --- | --- | --- | --- | --- | --- | --- | --- | --- |
|  | 1 | 2 | 3 | 4 | 5 | 6 | 1 | 2 | 3 | 4 | 5 |
| E-154 |  | 10 |  |  |  |  |  |  |  |  |  |
| ELM-120 |  |  | 10 |  |  |  |  |  |  |  |  |
| Hardening agent DDS | 23 | 27 | 23 | 27 | 26 | 23 | 19 | 24 | 26 | 19 | 22 |
| Solubility* | | | | | | | | | | | |
| Acetone | O | O | O | O | O | O | O | O | O | O | O |
| Methyl ethyl ketone | O | O | O | O | O | O | O | O | O | X | O |
| Toluene | O | O | O | O | O | O | O | O | O | X | O |
| Ethyl acetate | O | O | O | O | O | O | O | O | O | X | O |
| Tetrahydrofuran | O | O | O | O | O | O | O | O | O | O | O |
| Hardened product | | | | | | | | | | | |
| Glass transition point (°C.) | 200 | 210 | 202 | 200 | 200 | 200 | 180 | 202 | 185 | 203 | 190 |
| Elongation*** (%) | 6.0 | 5.2 | 5.4 | 5.2 | 5.5 | 6.0 | 5.5 | 4.0 | 5.3 | 4.8 | 5.5 |
| Elastic Modulus** (kg/mm$^2$) | 350 | 380 | 370 | 380 | 370 | 380 | 360 | 280 | 360 | 380 | 370 |
| water absorption rate (%) | 2.2 | 2.5 | 2.6 | 2.5 | 2.3 | 2.7 | 5.0 | 3.2 | 3.5 | 2.3 | 3.0 |

*20% resin solution - O (dissolved), X (precipitated)
**ASTM D-648
***JIS K-6911

While the invention has been described in detail and with reference to specific embodiment thereof, it will be apparent to one skilled in the art that various changes and modifications can be made therein without departing from the spirit and scope thereof.

What is claimed is:

1. An epoxy resin composition comprising
   (1) a mixture of epoxides of Components (A), (B) and (C)
   Component (A)
      20 to 60 wt% of an epoxy compound having a spiroacetal ring represented by the formula:

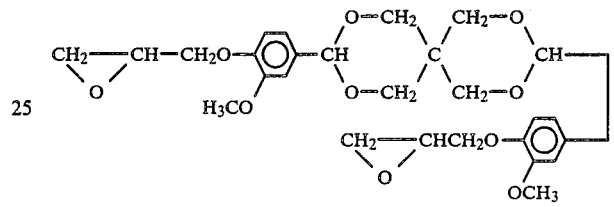

Component (B):
      10 to 50 wt% of a brominated epoxy resin
   Component (C):
      10 to 50 wt% of an epoxy resin selected from the group consisting of diglycidyl ether of bisphenol A, diglycidyl ether of bisphenol F, novolac type epoxy resins and N,N,O-triglycidyl-aminophenol type epoxy resins, and
   (2) a hardening agent.

2. The epoxy resin composition of claim 1, wherein said hardening agent is diaminodiphenylsulfone.

3. The epoxy resin composition of claim 1, wherein said Component (C) is a brominated phenol novolac resin.

* * * * *